(12) United States Patent
Fujiwara et al.

(10) Patent No.: US 6,344,567 B1
(45) Date of Patent: Feb. 5, 2002

(54) PROCESS FOR PRODUCING ASCORBIC ACID-2-PHOSPHORIC ESTER SALTS

(75) Inventors: Yoshio Fujiwara; Yuji Kobayashi; Makoto Saito, all of Kanagawa (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/629,169

(22) Filed: Jul. 31, 2000

Related U.S. Application Data
(60) Provisional application No. 60/217,382, filed on Jul. 11, 2000.

(30) Foreign Application Priority Data
Jul. 29, 1999 (JP) ............................................ 11-215649
Jul. 27, 2000 (JP) ........................................ 2000-227242

(51) Int. Cl.$^7$ .......................... C07F 9/02; C07D 307/30; C07D 307/62
(52) U.S. Cl. ....................................... 549/222; 549/315
(58) Field of Search ................................. 549/222, 315

(56) References Cited
U.S. PATENT DOCUMENTS

| | | | |
|---|---|---|---|
| 4,999,437 A | 3/1991 | Dobler et al. | 549/222 |
| 5,110,950 A | 5/1992 | Seib et al. | 549/222 |
| 5,210,220 A | 5/1993 | Pauling et al. | 549/222 |
| 5,420,302 A | 5/1995 | Kaiser et al. | 549/222 |

OTHER PUBLICATIONS

Chemical Abstracts, vol. 126, No. 24, Jun. 16, 1997 Columbus Ohio US; abstract No. 317553, Liu, Yulin et al: "Synthesis of magnesium L-ascorbate-2-phosphate" XP002149734 *Abstract* & Jingxi Huagong (1997); 14(2), 19–22.

*Primary Examiner*—T. A. Solola
(74) *Attorney, Agent, or Firm*—Sughrue Mion, PLLC

(57) ABSTRACT

A process for producing an ascorbic acid-2-phosphoric ester salt, where an ascorbic acid-2-phosphoric ester salt solution reduced in the content of excess phosphoric acid or a salt thereof mingled in the solution can be obtained from a solution containing an ascorbic acid-2-phosphoric ester or a salt thereof and a phosphoric acid or a salt thereof, with industrially high efficiency. A process for producing an alkaline earth metal salt of an ascorbic acid-2-phosphoric ester, comprising adding an alkaline earth metal compound to a stock solution containing an ascorbic acid-2-phosphoric ester or a salt thereof and a phosphoric acid or a salt thereof, at a liquid temperature of 0 to 30° C. to adjust the pH to 8.5 to 10.5.

8 Claims, No Drawings

PROCESS FOR PRODUCING ASCORBIC ACID-2-PHOSPHORIC ESTER SALTS

CROSS REFERENCE TO RELATED APPLICATIONS

This application is an application filed under 35 U.S.C. §111(a) claiming benefit pursuant to 35 U.S.C. §119(e)(1) of the filing date of Provisional Application No. 60/217,382 filed Jul. 11, 2000 pursuant to 35 U.S.C. §111(b).

FIELD OF THE INVENTION

The present invention relates to a process for producing an alkaline earth metal salt of an ascorbic acid-2-phosphoric ester, which is an ascorbic acid derivative useful as a cosmetic, a medical product or a food additive and widely used in various industrial fields including these.

BACKGROUND OF THE INVENTION

In general, ascorbic acid (vitamin C) is known to have various physiological and pharmacological activities.

For example, ascorbic acid is used as a whitening cosmetic because of its effect of preventing melamine pigmentation, or as an artificial feed additive for preventing cultured fish from vitamin C deficiency. However, the ascorbic acid is unstable in oxygen or heat and readily undergoes coloration or degradation. Therefore, ascorbic acid generally used is stabilized against oxygen, heat or the like by forming the hydroxyl group at the 2-position of an ascorbic acid into a phosphoric ester. More specifically, ascorbic acid widely used is a vitamin C derivative easily soluble in water, in the form of a salt, particularly magnesium salt, of an ascorbic acid-2-phosphoric ester.

The process for producing an ascorbic acid-2-phosphoric ester magnesium salt (hereinafter sometimes referred to as "APM") from an ascorbic acid-2-phosphoric ester (hereinafter sometimes referred to as "2-AP") using magnesium oxide, magnesium hydroxide, magnesium carbonate or the like is described in a large number of publications and patents such as JP-B-52-18181 (the term "JP-B" as used herein means an "examined Japanese patent publication"), JP-A-59-51293 (the term "JP-A" as used herein means an "unexamined published Japanese patent application") and JP-A-2-279690. However, specific conditions in the operation are not reported in detail.

JP-A-2-286693 describes a technique of adding magnesium oxide to an aqueous solution containing 2-AP obtained by phosphorylating 5,6-isopropylidene-L-ascorbic acid, while adjusting the pH using KOH to 8.5 to 9.0, separating the undissolved content by filtration, evaporation-concentrating the resulting solution, further crystallizing the solution with methanol, and filtering the solids obtained to produce APM.

However, in the case where APM is produced under the above-described conditions, excess phosphoric acid or a salt thereof is liable to intermingle in the product in a higher content or since the sedimentation of suspended matters is not completed within a short time, the filtration resistance increases and a washing operation is separately necessary. Thus, this technique is disadvantageous in the cumbersome process and also not satisfied in view of the cost.

In general, in the case of obtaining 2-AP by the phosphorylation reaction of an ascorbic acid, excess phosphoric acid, which is generated from the phosphorylating agent added and which cannot be completely removed in the purification step, remains in the solution obtained. This excess phosphoric acid reacts with a part of magnesium oxide added for the neutralization reaction of 2-AP and forms insoluble magnesium phosphate which is afterward separated by filtration and removed as an impurity. However, under conventional conditions, the magnesium phosphate cannot exhibit sufficiently high reactivity or precipitating property. Therefore, the excess phosphoric acid or magnesium phosphate intermingles in the solution of the step to adversely affect the product quality, and also a load is imposed on the filtering medium at the filtration of the residue, which is necessary in the next step.

SUMMARY OF THE INVENTION

The present invention has been made under these circumstances and provides a process for producing an ascorbic acid-2-phosphoric ester salt, where an ascorbic acid-2-phosphoric ester salt solution reduced in the content of excess phosphoric acid or a salt thereof mingled in the solution can be obtained from a solution containing an ascorbic acid-2-phosphoric ester or a salt thereof and a phosphoric acid or a salt thereof, with industrially high efficiency.

As a result of extensive investigations to solve the above-described problems, the present inventors have found that when an alkaline earth metal compound is added to a solution containing an ascorbic acid-2-phosphoric ester or a salt thereof and also containing phosphoric acid or a salt thereof, under a predetermined temperature condition to have a pH within a constant range, free phosphoric acid can be removed in the form of insoluble phosphoric acid alkaline earth metal having good precipitating property without imposing a load on the filtration medium. Thereby an ascorbic acid-2-phosphoric ester alkaline earth metal salt freed from any effect of the phosphoric acid contained on the quality can be produced efficiently.

More specifically, the present invention relates to the following embodiments:

(1) a process for producing an alkaline earth metal salt of an ascorbic acid-2-phosphoric ester, comprising adding an alkaline earth metal compound to a stock solution containing an ascorbic acid-2-phosphoric ester or a salt and a phosphoric acid or a salt thereof, at a liquid temperature of 0 to 30° C. to adjust the pH to 8.5 to 10.5;

(2) a process for producing an alkaline earth metal salt of an ascorbic acid-2-phosphoric ester as described in (1) above, which comprises a step of precipitating and separating the alkaline earth metal salt of phosphoric acid and recovering the supernatant;

(3) a process for producing an alkaline earth metal salt of an ascorbic acid-2-phosphoric ester as described in (2) above, which comprises precipitating and separating the alkaline earth metal salt of phosphoric acid and concentrating and crystallizing the supernatant recovered to obtain an alkaline earth metal salt of an ascorbic acid-2-phosphoric ester;

(4) a process for producing an alkaline earth metal salt of an ascorbic acid-2-phosphoric ester as described in any one of (1) to (3) above, wherein the molar ratio of the phosphoric acid or a salt thereof to the ascorbic acid-2-phosphoric ester or a salt thereof in the stock solution is from 0.02 to 0.5;

(5) a process for producing an alkaline earth metal salt of an ascorbic acid-2-phosphoric ester as described in any one of (1) to (4) above, wherein after the step of precipitating and separating the alkaline earth metal salt of phosphoric acid and recovering the supernatant, the molar ratio of the phosphoric acid or a salt thereof to the alkaline earth metal salt of an ascorbic acid-2-phosphoric ester in the supernatant is less than 0.02;

(6) a process for producing an alkaline earth metal salt of an ascorbic acid-2-phosphoric ester as described in any one of (1) to (5) above, wherein the alkaline earth metal is magnesium;

(7) a process for producing an alkaline earth metal salt of an ascorbic acid-2-phosphoric ester as described in any one of (1) to (6) above, wherein the alkaline earth metal compound is an oxide or hydroxide of an alkaline earth metal;

(8) a process for producing an alkaline earth metal salt of an ascorbic acid-2-phosphoric ester as described in any one of (1) to (7) above, wherein the stock solution has a pH of 3 or less.

DESCRIPTION OF THE PREFERRED EMBODIMENTS

The present invention is described in detail below.

The present invention relates to a process for producing an alkaline earth metal salt of an ascorbic acid-2-phosphoric ester, comprising adding an alkaline earth metal compound to a stock solution containing an ascorbic acid-2-phosphoric ester or a salt and also containing a phosphoric acid or a salt thereof, at a liquid temperature of 0 to 30° C. to adjust the pH to 8.5 to 10.5.

In the production process of an ascorbic acid-2-phosphoric ester alkaline earth metal salt of the present invention, the starting solution is not particularly limited as long as it is a solution containing 2-AP. Any of a 2-AP solution, a 2-AP alkali metal salt solution or a 2-AP alkaline earth metal salt solution may be used. For example, a 2-AP-containing solution obtained by directly phosphorylating ascorbic acid (see, JP-B-433-9219, JP-B-45-23746, JP-A-6-345786) and a 2-AP-containing solution obtained by phosphorylating 5,6-O-isopropylidene-L-ascorbic acid (see, JP-B-43-9219, JP-B-45-4497, JP-B-45-30328 and JP-B-59-4438) may be suitably used. In addition, a 2-AP-containing solution produced by the action of an enzyme or microorganism from an L-ascorbic acid and a phosphoric acid donor (see, JP-A-2-42996), and the like may also be used.

The 2-AP for use in the present invention is not particularly limited, and L-form 2-AP and DL-form 2-AP may be used. Among these, L-form 2-AP is preferred.

The stock solution used in the present invention means an aqueous solution containing phosphoric acid at a molar ratio $PO_4$/2-AP in the range from 0.02 to 0.5. If the molar ratio $PO_4$/2-AP is less than 0.02 or exceeds 0.5, the effect of the present invention is disadvantageously low.

In the case where the 2-AP is a salt or the 2-AP-containing solution contains an alkali metal or an alkaline earth metal, the solution is preferably decationized by treating it with an appropriate ion exchange resin. For the decationization, a general method may be used, such as a method where 2-AP is adsorbed to an ion exchange resin, eluted with from 0.1 to 2N dilute hydrochloric acid and then neutralized with an alkaline earth metal salt.

In the production process of the present invention, it is necessary to add an alkaline earth metal compound to a 2-AP solution at a liquid temperature of 0 to 30° C. to adjust the pH of 8.5 to 10.5. The temperature range of the 2-AP solution is suitably from 0 to 30° C., preferably from 5 to 25° C., more preferably from 10 to 20° C. If the liquid temperature is less than 0° C., freezing may occur and this is not preferred, whereas if it exceeds 30° C., the separability of insoluble impurities is disadvantageously deteriorated.

At the time when the addition of an alkaline earth metal compound is started, the pH is suitably 3 or less, preferably from 0.5 to 2. After the addition of the alkaline earth metal compound, the pH is suitably from 8.5 to 10.5, preferably from 9.0 to 10.5, more preferably from 9.0 to 10.0. If the pH after the addition of the alkaline earth metal compound is less than 8.5, the yield of APM disadvantageously decreases, whereas if it exceeds 10.5, the amount of unreacted alkaline earth metal compound increases and this is not preferred.

Even when the liquid temperature of the 2-AP solution is within the range from 0 to 30° C., if the pH deviates from the above-described range, for example, if the pH after the addition of the alkaline earth metal compound is less than 8.5, the phosphoric acid cannot be satisfactorily removed and this is not preferred. Furthermore, the precipitating property of insoluble matters disadvantageously decreases in the case where the 2-AP solution contains a large amount of phosphoric acid, which is an impurity if the liquid temperature deviates from the above-described range, for example, if the liquid temperature exceeds 30° C., even with a pH of 8.5 to 10.5.

Among the alkaline earth metal salts used in the present invention, a magnesium salt is preferred. Examples of magnesium include magnesium oxide, magnesium hydroxide and magnesium carbonate. Of these, magnesium oxide and magnesium hydroxide are preferred. In the present invention, when magnesium oxide is used for the neutralization reaction by an alkaline earth metal salt, the molar ratio of free phosphoric acid present in the solution during the step after the neutralization to APM becomes less than 0.02. Thereafter, undissolved matters are separated by filtration and the supernatant is recovered. This solution is concentrated and subsequently crystallized in an organic solvent, such as methanol, and the solids obtained are filtered. Then, APM is obtained.

In the present invention, after the undissolved matters as impurities are separated by filtration and the recovered supernatant is concentrated, the solution is crystallized by a conventionally known method to obtain the objective alkaline earth metal salt of 2-AP and the salt obtained is further dried and pulverized, whereby powdered 2-AP alkaline earth metal salt can be obtained.

As such, in the present invention, at the time of performing a neutralization reaction of the 2-AP salt by adding an alkaline earth metal compound, the solution temperature is controlled to a range from 0 to 30° C. and also the pH of 3 or less is adjusted to a range from 8.5 to 10.5, whereby an alkaline earth metal salt of 2-AP can be efficiently produced.

EXAMPLES

The present invention is described in greater detail below by referring to the Examples, however, the present invention is by no means limited to these Examples. Unless otherwise indicated therein, all parts, percents, ratios and the like are by weight.

Example 1

32 g of L-ascorbic acid-2-phosphoric ester magnesium salt was dissolved in 368 ml of pure water. The resulting solution was passed through a column packed with 2,000 ml of a strongly acidic cation exchange resin (Amberlite IR120B, produced by Organo) and then through 1,200 ml of pure water. As a result, 1,600 ml of a solution containing only 2-AP was obtained. This solution had a magnesium content of 1 ppm or less. To this solution, 1.0 g of 85% phosphoric acid was added to obtain an aqueous 2-AP solution containing phosphoric acid. The molar ratio of phosphoric acid to the 2-AP in this solution was 0.1.

While keeping the 2-AP solution temperature at 10° C., magnesium hydroxide was added to adjust the pH to 9.2 after the addition. The resulting solution was left standing for 4 hours and the supernatant was filtered to remove insoluble matters. At this time, the amount of phosphoric acid mingled in the aqueous APM solution was 0.01 in terms of the molar ratio of phosphoric acid to 2-AP.

The thus-obtained supernatant was concentrated by depressurization until the APM concentration reached 5% (w/v). A three-fold amount of methanol was added dropwise to this concentrated solution over 2 hours and the precipitated APM solids were collected by filtration and then dried under vacuum to obtain 26 g of APM.

Example 2

In a nitrogen atmosphere, 1,350 ml of pure water, 150 g of pyridine and 100 g of L-ascorbic acid were mixed and dissolved and after cooling the mixture solution to 0 to 10° C., an aqueous 10% sodium hydroxide solution was added to adjust the pH to about 12. While adding dropwise 150 g of phosphorus oxychloride and an aqueous 10% sodium hydroxide solution, the solution obtained was reacted at a pH of 12 and a liquid temperature kept at 0 to 10° C. After the completion of dropwise addition, the pH was adjusted to the vicinity of 7 by 35% hydrochloric acid and the pyridine was distilled off under reduced pressure. Thereafter, 35% hydrochloric acid was added to adjust the pH to 4.

This pH-adjusted solution was diluted with 6,500 ml of pure water, passed through a column packed with 2,000 ml of a medium basic anion exchange resin (Amberlite IRA-68, produced by Organo) and subsequently developed with 23,500 ml of 0.05N hydrochloric acid and then with 11,000 ml of 0.2N hydrochloric acid to obtain fractions containing 2-AP.

From this fraction aqueous solution, chlorine ion was removed to 500 ppm using an electrodialyser (Model DU-Ob, manufactured by Asahi Glass K. K.). In the dialyzed solution, the molar ratio of phosphate ion to 2-AP ion was 0.2. While keeping the temperature at 15° C., magnesium oxide was added to the dialyzed solution to adjust the pH after the addition to 10.1. This solution was left standing for 2 hours and the supernatant was filtered to remove insoluble matters. At this time, the amount of phosphoric acid mingled in the APM aqueous solution was 0.02 in terms of the molar ratio of phosphate ion to 2-AP ion.

The thus-obtained supernatant was treated in the same manner as in Example 1 to obtain powdered APM.

Comparative Example 1

An APM aqueous solution was obtained in the same manner as in Example 1 except that when the temperature of 2-AP solution was 34° C., magnesium hydroxide was added until the pH reached 7.8. After the supernatant was filtered to remove insoluble matters, the amount of phosphoric acid mingled in the APM aqueous solution was 0.04 in terms of the molar ratio of phosphoric acid to 2-AP.

According to the production process of the present invention, an ascorbic acid-2-phosphoric ester salt solution reduced in the content of excess phosphoric acid or a salt thereof mingled in the solution can be obtained from an aqueous solution containing an ascorbic acid-2-phosphoric ester or a salt thereof and also containing phosphoric acid or a salt thereof, with industrially high efficiency. The ascorbic acid-2-phosphoric ester alkaline earth metal salt obtained by the production process of the present invention is widely used as a cosmetic, a feed material, a medical product, a food additive or the like in various industrial fields.

While the invention has been described in detail and with reference to specific embodiments thereof, it will be apparent to one skilled in the art that various changes and modifications can be made therein without departing from the spirit and scope thereof.

What is claimed is:

1. A process for producing an alkaline earth metal salt of an ascorbic acid-2-phosphoric ester, comprising adding an alkaline earth metal compound to a stock solution containing an ascorbic acid-2-phosphoric ester or a salt thereof and a phosphoric acid or a salt thereof, at a liquid temperature of 0 to 30° C. to adjust the pH to 8.5 to 10.5.

2. The process for producing an alkaline earth metal salt of an ascorbic acid-2-phosphoric ester as claimed in claim 1, which comprises a step of precipitating and separating the alkaline earth metal salt of phosphoric acid and recovering the supernatant.

3. The process for producing an alkaline earth metal salt of an ascorbic acid-2-phosphoric ester as claimed in claim 2, which comprises precipitating and separating the alkaline earth metal salt of phosphoric acid and concentrating and crystallizing the supernatant recovered to obtain an alkaline earth metal salt of an ascorbic acid-2-phosphoric ester.

4. The process for producing an alkaline earth metal salt of an ascorbic acid-2-phosphoric ester as claimed in any one of claims 1 to 3, wherein the molar ratio of the phosphoric acid or a salt thereof to the ascorbic acid-2-phosphoric ester or a salt thereof in the stock solution is from 0.02 to 0.5.

5. The process for producing an alkaline earth metal salt of an ascorbic acid-2-phosphoric ester as claimed in any one of claims 1 to 3, wherein after the step of precipitating and separating the alkaline earth metal salt of phosphoric acid and recovering the supernatant, the molar ratio of the phosphoric acid or a salt thereof to the alkaline earth metal salt of an ascorbic acid-2-phosphoric ester in the supernatant is less than 0.02.

6. The process for producing an alkaline earth metal salt of an ascorbic acid-2-phosphoric ester as claimed in any one of claims 1 to 3, wherein the alkaline earth metal is magnesium.

7. The process for producing an alkaline earth metal salt of an ascorbic acid-2-phosphoric ester as claimed in any one of claims 1 to 3, wherein the alkaline earth metal compound is an oxide or hydroxide of an alkaline earth metal.

8. The process for producing an alkaline earth metal salt of an ascorbic acid-2-phosphoric ester as claimed in any one of claims 1 to 3, wherein the stock solution has a pH of 3 or less.

\* \* \* \* \*